United States Patent
Jaber et al.

(10) Patent No.: US 11,971,183 B2
(45) Date of Patent: Apr. 30, 2024

(54) SYSTEMS AND METHODS FOR REFRIGERANT LEAK DETECTION IN A CLIMATE CONTROL SYSTEM

(71) Applicant: Trane International Inc., Davidson, NC (US)

(72) Inventors: Youssef A. Jaber, Tyler, TX (US); Raymond Walter Rite, Tyler, TX (US)

(73) Assignee: Trane International Inc., Davidson, NC (US)

( * ) Notice: Subject to any disclaimer, the term of this patent is extended or adjusted under 35 U.S.C. 154(b) by 0 days.

(21) Appl. No.: 17/644,310

(22) Filed: Dec. 14, 2021

(65) Prior Publication Data
US 2022/0107106 A1    Apr. 7, 2022

Related U.S. Application Data

(63) Continuation of application No. 16/562,053, filed on Sep. 5, 2019.

(51) Int. Cl.
*F24F 11/36* (2018.01)
*F24F 11/89* (2018.01)
*G01N 29/024* (2006.01)
*G01N 33/00* (2006.01)

(52) U.S. Cl.
CPC .............. *F24F 11/36* (2018.01); *F24F 11/89* (2018.01); *G01N 29/024* (2013.01); *G01N 33/0027* (2013.01)

(58) Field of Classification Search
CPC .......... F24F 11/36; F24F 11/20; G01N 29/024
See application file for complete search history.

(56) References Cited

U.S. PATENT DOCUMENTS

| | | |
|---|---|---|
| 3,766,844 A | 10/1973 | Donnelly et al. |
| 4,138,856 A | 2/1979 | Orlowski |
| 4,711,096 A | 12/1987 | Krantz |
| 4,879,546 A | 11/1989 | Dunham et al. |
| 4,896,052 A | 1/1990 | Morrison et al. |
| 4,987,769 A | 1/1991 | Peacock et al. |
| 5,060,507 A | 10/1991 | Urmson et al. |

(Continued)

FOREIGN PATENT DOCUMENTS

| | | |
|---|---|---|
| BR | 112019010410 A2 | 9/2019 |
| CA | 3065728 C | 6/2021 |

(Continued)

OTHER PUBLICATIONS

US 11,402,122 B2, 09/2022, Tsuji (withdrawn)

*Primary Examiner* — Nelson J Nieves
(74) *Attorney, Agent, or Firm* — WOMBLE BOND DICKINSON (US) LLP

(57) ABSTRACT

Refrigerant leak detection systems as well as related climate control systems and methods are disclosed herein. In an embodiment, the refrigerant leak detection system includes a transmitter configured to emit an acoustic wave, and a receiver configured to detect the acoustic wave. The transmitter and the receiver are mounted within a space outside a conduit configured to carry a refrigerant of a climate control system. In addition, the refrigerant leak detection system includes a controller coupled to the transmitter and the receiver. The controller is configured to: determine a time of flight for the acoustic wave between the transmitter and the receiver, and determine whether a refrigerant is present in the space based on the time of flight.

18 Claims, 6 Drawing Sheets

(56) References Cited

U.S. PATENT DOCUMENTS

| | | |
|---|---|---|
| 5,090,507 A | 2/1992 | Olson et al. |
| 5,264,368 A | 11/1993 | Clarke et al. |
| 5,325,703 A | 7/1994 | Magori |
| 5,473,934 A | 12/1995 | Cobb |
| 5,710,377 A | 1/1998 | Youngquist et al. |
| 5,742,066 A | 4/1998 | Cavestri |
| 5,820,262 A | 10/1998 | Lechner |
| 5,918,475 A | 7/1999 | Sakakibara |
| 5,955,670 A | 9/1999 | Goodman et al. |
| 6,085,531 A | 7/2000 | Numoto |
| 6,279,378 B1 | 8/2001 | Sheen et al. |
| 6,471,136 B1 | 10/2002 | Chatterjee et al. |
| 6,644,047 B2 | 11/2003 | Taira |
| 6,655,161 B1 | 12/2003 | Koo |
| 6,701,722 B1 | 3/2004 | Seo |
| 6,742,384 B2 | 6/2004 | Avila |
| 6,772,598 B1 | 8/2004 | Rinehart |
| 6,791,088 B1 | 9/2004 | Williams, II |
| 6,889,537 B2 | 5/2005 | Anderson |
| 7,143,591 B2 | 12/2006 | Nonaka |
| 7,181,954 B2 | 2/2007 | Horie |
| 7,631,508 B2 | 12/2009 | Braun |
| 7,647,784 B2 | 1/2010 | Mizutani et al. |
| 7,752,853 B2 | 7/2010 | Singh |
| 7,814,757 B2 | 10/2010 | Zima |
| 7,946,121 B2 | 5/2011 | Yamaguchi et al. |
| 7,987,679 B2 | 8/2011 | Tanaka |
| 8,005,648 B2 | 8/2011 | Johnson |
| 8,070,355 B2 | 12/2011 | Minor |
| 8,180,495 B1 | 5/2012 | Roy |
| 8,302,414 B2 | 11/2012 | Hisaoka |
| 8,402,779 B2 | 3/2013 | Nishimura et al. |
| 8,570,179 B2 | 10/2013 | Holloway |
| 8,695,404 B2 | 4/2014 | Kadle |
| 8,786,437 B2 | 7/2014 | Breed |
| 8,899,099 B2 | 12/2014 | Grosse Bley |
| 9,164,519 B2 | 10/2015 | Holloway |
| 9,291,378 B2 | 3/2016 | Ueda et al. |
| 9,482,592 B2 | 11/2016 | Huseynov et al. |
| 9,541,319 B2 | 1/2017 | Morimoto |
| 9,568,227 B2 | 2/2017 | Douglas |
| 9,625,195 B2 | 4/2017 | Hiraki |
| 9,726,410 B2 | 8/2017 | Gao |
| 9,791,195 B2 | 10/2017 | Okada |
| 9,869,499 B2 | 1/2018 | Liu |
| 10,088,202 B2 | 10/2018 | Huff et al. |
| 10,126,012 B2 | 11/2018 | Ikawa |
| 10,126,031 B2 | 11/2018 | Shockley |
| 10,151,663 B2 | 12/2018 | Scancarello |
| 10,203,136 B2 | 2/2019 | Nishimura |
| 10,247,441 B2 | 4/2019 | Suzuki |
| 10,354,332 B2 | 7/2019 | Trainor |
| 10,399,412 B2 | 9/2019 | Mathe |
| 10,401,253 B2 | 9/2019 | Cooper et al. |
| 10,408,484 B2 | 9/2019 | Honda |
| 10,408,488 B2 | 9/2019 | Suzuki |
| 10,416,113 B2 | 9/2019 | Chen et al. |
| 10,424,190 B2 | 9/2019 | Zribi et al. |
| 10,458,689 B2 | 10/2019 | Suzuki |
| 10,479,170 B2 | 11/2019 | Enomoto et al. |
| 10,480,807 B2 | 11/2019 | Goel |
| 10,488,066 B2 | 11/2019 | Honda |
| 10,488,072 B2 | 11/2019 | Yajima |
| 10,508,847 B2 | 12/2019 | Yajima |
| 10,539,358 B2 | 1/2020 | Suzuki |
| 10,557,648 B2 | 2/2020 | Naito |
| 10,584,890 B2 | 3/2020 | Steinberg |
| 10,605,505 B2 | 3/2020 | Appler et al. |
| 10,634,404 B2 | 4/2020 | Obara |
| 10,641,268 B2 | 5/2020 | Brostrom et al. |
| 10,655,884 B2 | 5/2020 | Iura |
| 10,677,679 B2 | 6/2020 | Gupte |
| 10,712,035 B2 | 7/2020 | Yamada |
| 10,714,772 B2 | 7/2020 | Nishida et al. |
| 10,724,766 B2 | 7/2020 | Suzuki |
| 10,767,881 B2 | 9/2020 | Wang |
| 10,767,882 B2 | 9/2020 | Kowald |
| 10,782,040 B2 | 9/2020 | Wacker |
| 10,808,960 B2 | 10/2020 | Suzuki |
| 10,816,232 B2 | 10/2020 | Crawford |
| 10,816,247 B2 | 10/2020 | McQuade |
| 10,823,445 B2 | 11/2020 | Suzuki |
| 10,928,091 B2 | 2/2021 | Crawford |
| 10,935,454 B2 | 3/2021 | Kester |
| 10,941,956 B2 | 3/2021 | Gao |
| 10,996,131 B2 | 5/2021 | McQuade |
| 11,002,467 B2 | 5/2021 | Wada |
| 11,015,828 B2 | 5/2021 | Sakae |
| 11,015,834 B2 | 5/2021 | Kageyama |
| 11,015,852 B2 | 5/2021 | Sakae |
| 11,022,346 B2 | 6/2021 | Sun |
| 11,041,647 B2 | 6/2021 | Weinert |
| 11,041,666 B2 | 6/2021 | Sakae |
| 11,067,303 B2 | 7/2021 | Obara |
| 11,067,321 B2 | 7/2021 | Suzuki |
| 11,079,149 B2 | 8/2021 | Papas |
| 11,079,300 B2 | 8/2021 | Shi |
| 11,092,566 B2 | 8/2021 | Chen |
| 11,098,915 B2 | 8/2021 | Crawford |
| 11,117,449 B2 | 9/2021 | Renault |
| 11,118,821 B2 | 9/2021 | Matsuda |
| 11,118,822 B2 | 9/2021 | Kujak |
| 11,125,457 B1 | 9/2021 | Alfano |
| 11,131,470 B2 | 9/2021 | Minamida |
| 11,137,184 B2 | 10/2021 | Yamada et al. |
| 11,143,439 B2 | 10/2021 | Matsuda |
| 11,150,156 B2 | 10/2021 | Nanba |
| 11,162,725 B2 | 11/2021 | Suzuki |
| 11,175,060 B2 | 11/2021 | Mowris |
| 11,199,337 B2 | 12/2021 | Kawashima |
| 11,231,199 B2 | 1/2022 | Ikeda |
| 11,248,816 B2 | 2/2022 | Ikawa |
| 11,260,728 B2 | 3/2022 | Kondrk |
| 11,262,097 B2 | 3/2022 | Suzuki |
| 11,268,718 B2 | 3/2022 | Minamida |
| 11,274,866 B2 | 3/2022 | Yamada |
| 11,274,871 B2 | 3/2022 | Sakae |
| 11,280,507 B2 | 3/2022 | Yoneyama |
| 11,280,523 B2 | 3/2022 | Sakae |
| 11,293,674 B2 | 4/2022 | Yamada |
| 11,306,954 B2 | 4/2022 | Arensmeier |
| 11,346,570 B2 | 5/2022 | Yoshimi |
| 11,353,247 B2 | 6/2022 | Bernhardt |
| 11,359,846 B2 | 6/2022 | Welch |
| 11,378,313 B2 | 7/2022 | Goel |
| 11,378,316 B2 | 7/2022 | Walser |
| 11,407,287 B2 | 8/2022 | Repice |
| 11,408,624 B2 | 8/2022 | Hovardas |
| 11,428,435 B2 | 8/2022 | Eskew |
| 11,435,102 B2 | 9/2022 | Watanabe |
| 11,435,124 B2 | 9/2022 | Kondrk |
| 11,441,803 B2 | 9/2022 | Goel |
| 11,441,813 B2 | 9/2022 | Tsuji |
| 11,441,820 B2 | 9/2022 | Weyna |
| 11,472,265 B2 | 10/2022 | Stockbridge |
| 11,506,411 B2 | 11/2022 | Shirai |
| 11,530,830 B2 | 12/2022 | Watanabe |
| 11,536,502 B2 | 12/2022 | Yajima |
| 11,573,149 B2 | 2/2023 | Gupte |
| 11,578,887 B2 | 2/2023 | Delgoshaei |
| 11,598,560 B2 | 3/2023 | Yajima |
| 11,604,019 B2 | 3/2023 | Alfano |
| 11,604,156 B2 | 3/2023 | Chen |
| 11,609,009 B2 | 3/2023 | Blanton |
| 11,609,031 B2 | 3/2023 | Matsuda |
| 11,609,032 B2 | 3/2023 | Butler |
| 11,609,046 B2 | 3/2023 | Thobias |
| 11,614,249 B2 | 3/2023 | Chen |
| 11,635,339 B2 | 4/2023 | Willett |
| 11,644,225 B2 | 5/2023 | Delgoshaei |
| 11,674,727 B2 | 6/2023 | De |
| 2002/0178738 A1 | 12/2002 | Taira et al. |
| 2004/0168505 A1 | 9/2004 | Dudley |
| 2008/0295580 A1 | 12/2008 | Minor |

(56) References Cited

U.S. PATENT DOCUMENTS

| | | |
|---|---|---|
| 2009/0107157 A1 | 4/2009 | Dube |
| 2011/0112814 A1 | 5/2011 | Clark |
| 2013/0021159 A1 | 1/2013 | Timm |
| 2013/0213068 A1 | 8/2013 | Goel |
| 2016/0245566 A1 | 8/2016 | Hiraki et al. |
| 2017/0122833 A1 | 5/2017 | Furry |
| 2018/0087815 A1 | 3/2018 | Kujak et al. |
| 2018/0259235 A1 | 9/2018 | Delgoshaei |
| 2018/0327179 A1 | 11/2018 | Papas |
| 2019/0011325 A1 | 1/2019 | Nanba et al. |
| 2019/0133341 A1 | 5/2019 | Fischer |
| 2019/0170384 A1 | 6/2019 | Mcquade |
| 2019/0170599 A1 | 6/2019 | Kester |
| 2019/0170600 A1 | 6/2019 | Tice |
| 2019/0170603 A1 | 6/2019 | Gupte |
| 2019/0195542 A1 | 6/2019 | Hansen et al. |
| 2019/0195550 A1 | 6/2019 | Sakae et al. |
| 2019/0204289 A1 | 7/2019 | Wrobel |
| 2019/0240289 A1 | 8/2019 | Hohlbaum et al. |
| 2019/0264963 A1 | 8/2019 | Kondrk |
| 2019/0316820 A1 | 10/2019 | Zhai |
| 2019/0316821 A1 | 10/2019 | Zhai et al. |
| 2019/0390877 A1 | 12/2019 | Sakae et al. |
| 2020/0011560 A1 | 1/2020 | Minamida |
| 2020/0033036 A1 | 1/2020 | Yamada et al. |
| 2020/0049361 A1 | 2/2020 | Minamida et al. |
| 2020/0110000 A1 | 4/2020 | Roth |
| 2020/0124493 A1 | 4/2020 | Duerr |
| 2020/0166470 A1 | 5/2020 | Chen et al. |
| 2020/0182734 A1 | 6/2020 | Ueno et al. |
| 2020/0208861 A1 | 7/2020 | Chen |
| 2020/0232685 A1 | 7/2020 | Swab |
| 2020/0240869 A1 | 7/2020 | Yesh et al. |
| 2020/0263891 A1 | 8/2020 | Noor |
| 2020/0271344 A1 | 8/2020 | Ikeda et al. |
| 2020/0300522 A1 | 9/2020 | Inao |
| 2020/0309434 A1 | 10/2020 | Walser et al. |
| 2020/0324624 A1 | 10/2020 | Repice et al. |
| 2020/0355420 A1 | 11/2020 | Goel et al. |
| 2020/0386431 A1 | 12/2020 | Kondrk |
| 2020/0393140 A1 | 12/2020 | Nouchi |
| 2021/0001689 A1 | 1/2021 | Kondrk et al. |
| 2021/0018199 A1 | 1/2021 | Blanton |
| 2021/0071887 A1 | 3/2021 | Jaber et al. |
| 2021/0095876 A1 | 4/2021 | Branson et al. |
| 2021/0095887 A1 | 4/2021 | Kilgo |
| 2021/0108819 A1 | 4/2021 | Chen |
| 2021/0108857 A1 | 4/2021 | Thobias et al. |
| 2021/0123624 A1 | 4/2021 | Kronstrom |
| 2021/0131696 A1 | 5/2021 | She et al. |
| 2021/0140650 A1 | 5/2021 | Wilson |
| 2021/0140662 A1 | 5/2021 | Goel et al. |
| 2021/0148620 A1 | 5/2021 | Yamada et al. |
| 2021/0164678 A1 | 6/2021 | Delgoshaei |
| 2021/0190353 A1 | 6/2021 | Blanton |
| 2021/0199359 A1 | 7/2021 | Grabon |
| 2021/0207830 A1 | 7/2021 | Chen |
| 2021/0207831 A1 | 7/2021 | Lord |
| 2021/0213802 A1 | 7/2021 | Poolman et al. |
| 2021/0215413 A1 | 7/2021 | Deaville |
| 2021/0229528 A1 | 7/2021 | Stockbridge |
| 2021/0247086 A1 | 8/2021 | Sasaki |
| 2021/0247096 A1 | 8/2021 | Hovardas |
| 2021/0268875 A1 | 9/2021 | Weyna et al. |
| 2021/0278128 A1 | 9/2021 | Scarcella |
| 2021/0285680 A1 | 9/2021 | Atchison et al. |
| 2021/0285840 A1 | 9/2021 | Willett |
| 2021/0293430 A1 | 9/2021 | Yamada |
| 2021/0293431 A1 | 9/2021 | Delgoshaei |
| 2021/0293446 A1 | 9/2021 | Fard |
| 2021/0302056 A1 | 9/2021 | Eskew et al. |
| 2021/0310678 A1 | 10/2021 | Weinert |
| 2021/0348820 A1 | 11/2021 | Kobayashi |
| 2021/0356150 A1 | 11/2021 | Green et al. |
| 2021/0356154 A1 | 11/2021 | Kobayashi |
| 2021/0356155 A1 | 11/2021 | Yoshimi et al. |
| 2021/0364180 A1 | 11/2021 | Chen |
| 2021/0396413 A1 | 12/2021 | Maddox |
| 2021/0396696 A1 | 12/2021 | Hornung |
| 2021/0404685 A1 | 12/2021 | Butler |
| 2022/0003443 A1 | 1/2022 | Kobayashi |
| 2022/0003471 A1 | 1/2022 | Welch |
| 2022/0003472 A1 | 1/2022 | Okuda |
| 2022/0034568 A1 | 2/2022 | Satou |
| 2022/0042698 A1 | 2/2022 | Butler |
| 2022/0057100 A1 | 2/2022 | Ikeda |
| 2022/0065832 A1 | 3/2022 | Oggianu |
| 2022/0082304 A1 | 3/2022 | Welch |
| 2022/0090979 A1 | 3/2022 | Kester |
| 2022/0099346 A1 | 3/2022 | Alfano |
| 2022/0128253 A1 | 4/2022 | Suzuki |
| 2022/0128277 A1 | 4/2022 | Fukuyama |
| 2022/0128278 A1 | 4/2022 | Parker |
| 2022/0128281 A1 | 4/2022 | Tsuji |
| 2022/0134844 A1 | 5/2022 | Palmisano |
| 2022/0146132 A1 | 5/2022 | McQuade |
| 2022/0170654 A1 | 6/2022 | Delgoshaei |
| 2022/0186960 A1 | 6/2022 | Hirai |
| 2022/0221184 A1 | 7/2022 | Gupta |
| 2021/0108820 A1 | 8/2022 | Hovardas |
| 2022/0243938 A1 | 8/2022 | Notaro |
| 2022/0243939 A1 | 8/2022 | Notaro |
| 2022/0243940 A1 | 8/2022 | Notaro |
| 2022/0243941 A1 | 8/2022 | Notaro |
| 2022/0252291 A1 | 8/2022 | Alfano |
| 2022/0252304 A1 | 8/2022 | Green |
| 2022/0297510 A1 | 9/2022 | Kondrk |
| 2022/0307711 A1 | 9/2022 | Lord |
| 2022/0307740 A1 | 9/2022 | Lord |
| 2022/0307937 A1 | 9/2022 | Thyssen |
| 2022/0341612 A1 | 10/2022 | West |
| 2022/0341804 A1 | 10/2022 | West |
| 2022/0349600 A1 | 11/2022 | Alfano |
| 2022/0397297 A1 | 12/2022 | Foster |
| 2023/0009291 A1 | 1/2023 | Hjortland |
| 2023/0032795 A1 | 2/2023 | Sunderland |
| 2023/0048352 A1 | 2/2023 | Wright |
| 2023/0058790 A1 | 2/2023 | Rumler |
| 2023/0085125 A1 | 3/2023 | Yamaguchi |
| 2023/0107694 A1 | 4/2023 | Kawano |
| 2023/0109334 A1 | 4/2023 | Welch |
| 2023/0117306 A1 | 4/2023 | Petele |

FOREIGN PATENT DOCUMENTS

| | | |
|---|---|---|
| CN | 204043134 U | 12/2014 |
| CN | 110375466 A | 10/2019 |
| CN | 110375467 A | 10/2019 |
| CN | 110646362 A | 1/2020 |
| CN | 109073262 B | 8/2020 |
| DE | 102019205908 A1 | 10/2020 |
| DE | 102017217685 B4 | 10/2021 |
| EP | 0148591 B1 | 2/1988 |
| EP | 0783099 A1 | 7/1997 |
| EP | 1792571 A1 | 6/2007 |
| EP | 2354724 A3 | 11/2014 |
| EP | 3054231 B1 | 7/2018 |
| EP | 3374701 A1 | 9/2018 |
| EP | 3457044 A4 | 5/2019 |
| EP | 3460347 A4 | 5/2019 |
| EP | 3428554 B1 | 7/2019 |
| EP | 3425295 B1 | 9/2019 |
| EP | 3321607 B1 | 12/2019 |
| EP | 3405629 A4 | 1/2020 |
| EP | 3683518 A1 | 7/2020 |
| EP | 3693687 A3 | 10/2020 |
| EP | 3730854 A1 | 10/2020 |
| EP | 3751209 A1 | 12/2020 |
| EP | 3534084 B1 | 2/2021 |
| EP | 3584522 B1 | 4/2021 |
| EP | 3798527 A4 | 5/2021 |
| EP | 3816542 A1 | 5/2021 |
| EP | 3040654 B1 | 6/2021 |
| EP | 3875861 A1 | 9/2021 |

(56) References Cited

FOREIGN PATENT DOCUMENTS

| | | |
|---|---|---|
| EP | 3901526 A1 | 10/2021 |
| EP | 3901530 A1 | 10/2021 |
| EP | 3859223 A4 | 11/2021 |
| EP | 3859249 A4 | 11/2021 |
| EP | 3906382 A1 | 11/2021 |
| EP | 3911931 A2 | 11/2021 |
| EP | 3686520 B1 | 12/2021 |
| EP | 3919837 A1 | 12/2021 |
| EP | 3943858 A1 | 1/2022 |
| EP | 3961119 A1 | 3/2022 |
| EP | 3974032 A1 | 3/2022 |
| EP | 4033165 A1 | 7/2022 |
| EP | 3279580 B1 | 9/2022 |
| EP | 3869122 B1 | 11/2022 |
| EP | 4160101 A1 | 4/2023 |
| ES | 2804267 T3 | 2/2021 |
| FR | 3102237 A1 | 4/2021 |
| FR | 3111418 A1 | 12/2021 |
| JP | 20000249435 A | 9/2000 |
| JP | 2002092714 A | 3/2002 |
| JP | 2002206984 A | 7/2002 |
| JP | 2002263445 A | 9/2002 |
| JP | 2003161551 A | 6/2003 |
| JP | 2006158411 A | 6/2006 |
| JP | 2007127316 A | 5/2007 |
| JP | 2008064453 A | 3/2008 |
| JP | 2010210129 A | 9/2010 |
| JP | 2014035171 A | 2/2014 |
| JP | 2014035171 A | 11/2014 |
| JP | 6466219 B2 | 1/2019 |
| JP | 6466219 B2 | 2/2019 |
| JP | 6528446 B2 | 6/2019 |
| JP | WO2019016959 A1 | 7/2019 |
| JP | 6557329 B2 | 8/2019 |
| JP | 2018167861 A1 | 11/2019 |
| JP | 6628833 B2 | 1/2020 |
| JP | 6656363 B2 | 3/2020 |
| JP | 6701337 B2 | 5/2020 |
| JP | 2020515850 A | 5/2020 |
| JP | 2020130326 A | 8/2020 |
| JP | 6766638 B2 | 10/2020 |
| JP | 6766639 B2 | 10/2020 |
| JP | 2020169798 A | 10/2020 |
| JP | 6779355 B2 | 11/2020 |
| JP | 2020183829 A | 11/2020 |
| JP | 2021075076 A | 5/2021 |
| JP | 6931093 B2 | 9/2021 |
| JP | 2021131182 A | 9/2021 |
| JP | 2021131194 A | 9/2021 |
| JP | 2021131200 A | 9/2021 |
| JP | WO2020194490 A1 | 11/2021 |
| KR | 20140100341 A | 8/2014 |
| KR | 101609677 B1 | 4/2016 |
| KR | 20190009713 A | 1/2019 |
| KR | 20190058448 A | 5/2019 |
| KR | 20160066367 A | 6/2019 |
| KR | 20210001769 A | 1/2021 |
| KR | 20210042970 A | 4/2021 |
| MX | 2019011319 A | 3/2016 |
| RU | 2720037 C2 | 4/2020 |
| WO | 2010007448 A1 | 1/2010 |
| WO | 2014160831 A1 | 10/2014 |
| WO | 2017002215 A1 | 1/2017 |
| WO | 2020010082 A1 | 1/2020 |
| WO | 2021260588 A1 | 12/2021 |
| WO | 2022244177 A1 | 11/2022 |
| WO | 2022264368 A1 | 12/2022 |

SYSTEMS AND METHODS FOR REFRIGERANT LEAK DETECTION IN A CLIMATE CONTROL SYSTEM

CROSS-REFERENCE TO RELATED APPLICATIONS

The present application is a continuation of application Ser. No. 16/562,053, filed Sep. 5, 2019, by Jaber, et al., entitled "Systems and Methods for Refrigerant Leak Detection in a Climate Control System," which is hereby incorporated by reference in its entirety.

STATEMENT REGARDING FEDERALLY SPONSORED RESEARCH OR DEVELOPMENT

Not applicable.

BACKGROUND

A climate control system, such as a heating, ventilation, and air conditioning (HVAC) system a dehumidification system, a refrigeration system, etc., may circulate a refrigerant so as to transfer heat out of and/or into an indoor or interior space. The refrigerant is separated from the air flowing within and through the indoor space by one or more conduits (e.g., tubing, coils, etc.). In some circumstances, the refrigerant may be toxic and/or flammable such that a leak of the refrigerant may pose a safety issue. In addition, regardless of the toxicity and/or flammability of the refrigerant, a loss of the refrigerant due to a leak may prevent the climate control system from effectively transferring heat from and/or into the indoor space during operations.

BRIEF SUMMARY

Some embodiments disclosed herein are directed to a refrigerant leak detection system for a climate control system. In an embodiment, the refrigerant leak detection system includes a transmitter configured to emit an acoustic wave, and a receiver configured to detect the acoustic wave. The transmitter and the receiver are mounted within a space outside a conduit configured to carry a refrigerant of the climate control system. In addition, the refrigerant leak detection system includes a controller coupled to the transmitter and the receiver. The controller is configured to: determine a time of flight for the acoustic wave between the transmitter and the receiver, and determine a time of flight for the acoustic wave between the transmitter and the receiver.

Other embodiments disclosed herein are directed to a climate control system. In an embodiment, the climate control system includes a heat exchanger comprising a conduit to flow refrigerant therethrough. In addition, the climate control system includes a refrigerant leak detection system coupled to the heat exchanger. The refrigerant leak detection system includes a transmitter configured to emit an acoustic wave, and a receiver configured to detect the acoustic wave. The transmitter and the receiver are mounted within a space outside the conduit. In addition, the refrigerant leak detection system includes a controller coupled to the transmitter and the receiver. The controller is configured to: determine a time of flight for the acoustic wave between the transmitter and the receiver, and determine whether a refrigerant is present in the space based on the time of flight.

Still other embodiments disclosed herein are directed to a method of detecting a refrigerant leak from a climate control system. In an embodiment, the method includes (a) emitting an acoustic wave into a space outside of a conduit of the climate control system. In addition, the method includes (b) receiving the acoustic wave. Further, the method includes (c) determining a time of flight between (a) and (b). Still further, the method includes (d) determining that refrigerant is within the space as a result of the time of flight.

Embodiments described herein comprise a combination of features and characteristics intended to address various shortcomings associated with certain prior devices, systems, and methods. The foregoing has outlined rather broadly the features and technical characteristics of the disclosed embodiments in order that the detailed description that follows may be better understood. The various characteristics and features described above, as well as others, will be readily apparent to those skilled in the art upon reading the following detailed description, and by referring to the accompanying drawings. It should be appreciated that the conception and the specific embodiments disclosed may be readily utilized as a basis for modifying or designing other structures for carrying out the same purposes as the disclosed embodiments. It should also be realized that such equivalent constructions do not depart from the spirit and scope of the principles disclosed herein.

BRIEF DESCRIPTION OF THE DRAWINGS

For a detailed description of various exemplary embodiments, reference will now be made to the accompanying drawings in which.

DETAILED DESCRIPTION

Figure 1:
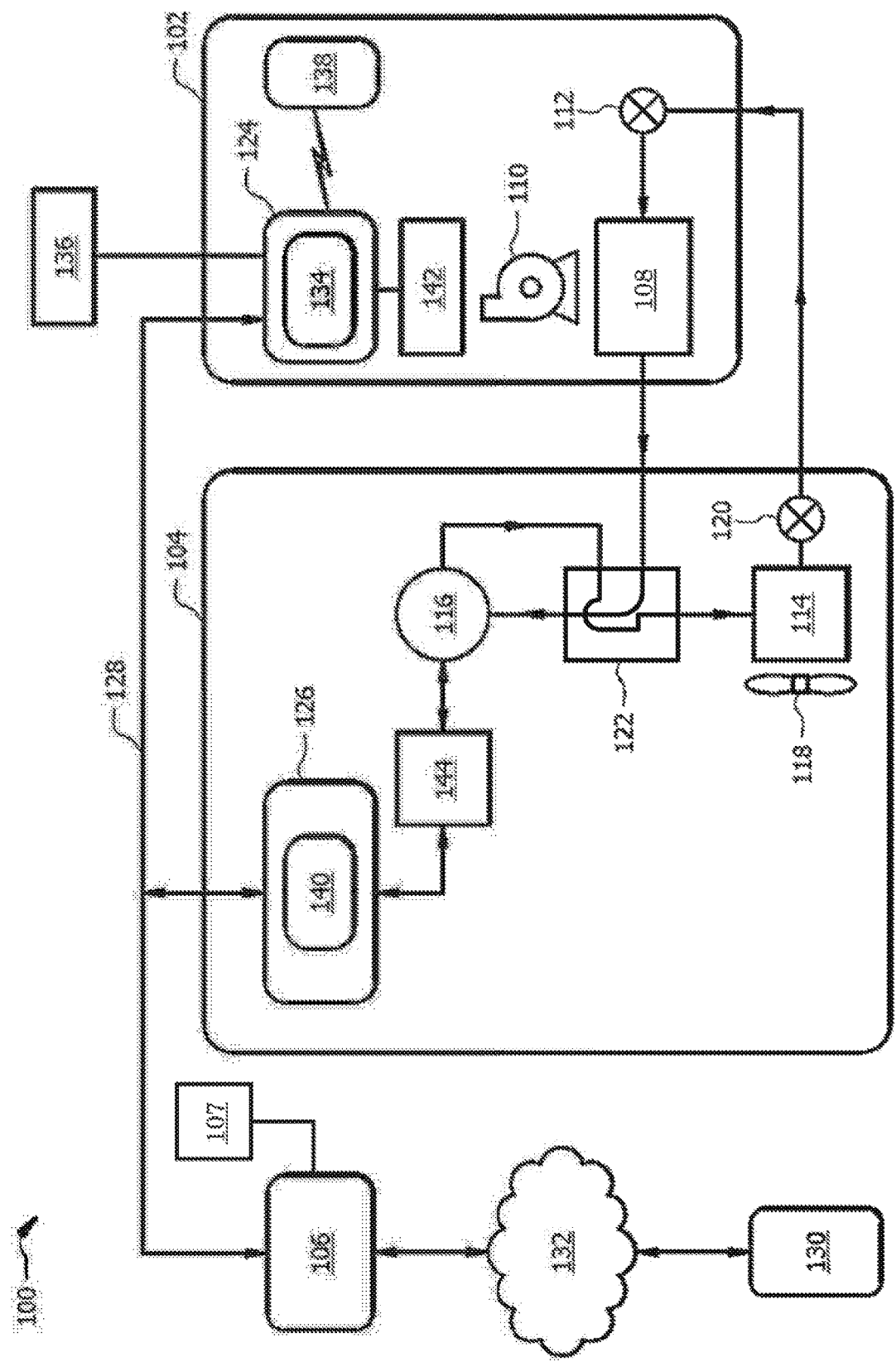
FIG. 1 is a diagram of a HVAC system configured for operating in a cooling mode according to some embodiments.

The following discussion is directed to various exemplary embodiments. However, one of ordinary skill in the art will understand that the examples disclosed herein have broad application, and that the discussion of any embodiment is meant only to be exemplary of that embodiment, and not intended to suggest that the scope of the disclosure, including the claims, is limited to that embodiment.

The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection of the two devices, or through an indirect connection that is established via other devices, components, nodes, and connections. In addition, as used herein, the terms "axial" and "axially" generally mean along or parallel to a given axis (e.g., central axis of a body or a port), while the terms "radial" and "radially" generally mean perpendicular to the given axis. For instance, an axial distance refers to a distance measured along or parallel to the axis, and a radial distance means a distance measured perpendicular to the axis. Further, when used herein (including in the claims), the words "about," "generally," "substantially," "approximately," and the like mean within a range of plus or minus 10% unless otherwise stated herein.

As previously described, a leak of refrigerant from a climate control system may be problematic for a number of reasons. As a result, it may be desirable to detect leaks within a climate control system during operations, so as to more quickly alert personnel, residents, system controllers, etc. Accordingly, embodiments disclosed herein include systems and methods for detecting a refrigerant leak from a climate control system. As described in more detail below, the systems and methods disclosed herein may determine the presence of a leak by monitoring the speed of sound through a space proximate to a refrigerant-containing conduit of the climate control system (or a time of flight of acoustic waves traveling through the space). Accordingly, through use of the disclosed systems and methods, a refrigerant leak may be detected such that appropriate actions (e.g., repairs, system operations, etc.) may take place so as to avoid or reduce the negative consequences associated with such a leak.

Referring now to FIG. 1, a schematic diagram of a climate control system 100 according to some embodiments is shown. In this embodiment, climate control system 100 is an HVAC system, and thus, system 100 may be referred to herein as HVAC system 100. However, it should be appreciated that the systems and methods disclosed herein may be utilized within a wide variety of climate control systems, such as, for instance, dehumidification systems, refrigeration systems, air conditioning systems, etc. Most generally, HVAC system 100 comprises a heat pump system that may be selectively operated to implement one or more substantially closed thermodynamic refrigeration cycles to provide a cooling functionality (hereinafter "cooling mode") and/or a heating functionality (hereinafter "heating mode"). The HVAC system 100, configured as a heat pump system, generally comprises an indoor unit 102, an outdoor unit 104, and a system controller 106 that may generally control operation of the indoor unit 102 and/or the outdoor unit 104.

Indoor unit 102 generally comprises an indoor air handling unit (e.g., such as air unit 150 described below) comprising an indoor heat exchanger 108, an indoor fan 110, an indoor metering device 112, and an indoor controller 124. The indoor heat exchanger 108 may generally be configured to promote heat exchange between refrigerant carried within internal tubing of the indoor heat exchanger 108 and an airflow that may contact the indoor heat exchanger 108 but that is segregated from the refrigerant. In some embodiments, the indoor heat exchanger 108 may comprise a plate-fin heat exchanger. However, in other embodiments, indoor heat exchanger 108 may comprise a microchannel heat exchanger and/or any other suitable type of heat exchanger.

The indoor fan 110 may generally comprise a centrifugal blower comprising a blower housing, a blower impeller at least partially disposed within the blower housing, and a blower motor configured to selectively rotate the blower impeller. The indoor fan 110 may generally be configured to provide airflow through the indoor unit 102 and/or the indoor heat exchanger 108 to promote heat transfer between the airflow and a refrigerant flowing through the indoor heat exchanger 108. The indoor fan 110 may also be configured to deliver temperature-conditioned air from the indoor unit 102 to one or more areas and/or zones of an indoor space. The indoor fan 110 may generally comprise a mixed-flow fan and/or any other suitable type of fan. The indoor fan 110 may generally be configured as a modulating and/or variable speed fan capable of being operated at many speeds over one or more ranges of speeds. In other embodiments, the indoor fan 110 may be configured as a multiple speed fan capable of being operated at a plurality of operating speeds by selectively electrically powering different ones of multiple electromagnetic windings of a motor of the indoor fan 110. In yet other embodiments, however, the indoor fan 110 may be a single speed fan.

The indoor metering device 112 may generally comprise an electronically-controlled motor-driven electronic expansion valve (EEV). In some embodiments, however, the indoor metering device 112 may comprise a thermostatic expansion valve, a capillary tube assembly, and/or any other suitable metering device. In some embodiments, while the indoor metering device 112 may be configured to meter the volume and/or flow rate of refrigerant through the indoor metering device 112, the indoor metering device 112 may also comprise and/or be associated with a refrigerant check valve and/or refrigerant bypass configuration when the direction of refrigerant flow through the indoor metering device 112 is such that the indoor metering device 112 is not intended to meter or otherwise substantially restrict flow of the refrigerant through the indoor metering device 112.

Outdoor unit 104 generally comprises an outdoor heat exchanger 114, a compressor 116, an outdoor fan 118, an outdoor metering device 120, a reversing valve 122, and an outdoor controller 126. In some embodiments, outdoor unit 104 may comprise an outdoor air handling unit (e.g., such as air unit 150 described below) including outdoor heat exchanger 114 and outdoor fan 118. In some embodiments, the outdoor unit 104 may also comprise a plurality of temperature sensors for measuring the temperature of the outdoor heat exchanger 114, the compressor 116, and/or the outdoor ambient temperature. The outdoor heat exchanger 114 may generally be configured to promote heat transfer between a refrigerant carried within internal passages or tubing of the outdoor heat exchanger 114 and an airflow that contacts the outdoor heat exchanger 114 but that is segregated from the refrigerant. In some embodiments, outdoor heat exchanger 114 may comprise a plate-fin heat exchanger. However, in other embodiments, outdoor heat exchanger 114 may comprise a spine-fin heat exchanger, a microchannel heat exchanger, or any other suitable type of heat exchanger.

The compressor 116 may generally comprise a variable speed scroll-type compressor that may generally be configured to selectively pump refrigerant at a plurality of mass flow rates through the indoor unit 102, the outdoor unit 104, and/or between the indoor unit 102 and the outdoor unit 104. In some embodiments, the compressor 116 may comprise a rotary type compressor configured to selectively pump refrigerant at a plurality of mass flow rates. In some embodiments, however, the compressor 116 may comprise a modulating compressor that is capable of operation over a plurality of speed ranges, a reciprocating-type compressor, a single speed compressor, and/or any other suitable refrigerant compressor and/or refrigerant pump. In some embodiments, the compressor 116 may be controlled by a compressor drive controller 144, also referred to as a compressor drive and/or a compressor drive system.

The outdoor fan 118 may generally comprise an axial fan comprising a fan blade assembly and fan motor configured to selectively rotate the fan blade assembly. The outdoor fan 118 may generally be configured to provide airflow through the outdoor unit 104 and/or the outdoor heat exchanger 114 to promote heat transfer between the airflow and a refrigerant flowing through the indoor heat exchanger 108. The outdoor fan 118 may generally be configured as a modulating and/or variable speed fan capable of being operated at a plurality of speeds over a plurality of speed ranges. In other embodiments, the outdoor fan 118 may comprise a mixed-flow fan, a centrifugal blower, and/or any other suitable type of fan and/or blower, such as a multiple speed fan capable of being operated at a plurality of operating speeds by selectively electrically powering different multiple electromagnetic windings of a motor of the outdoor fan 118. In yet other embodiments, the outdoor fan 118 may be a single speed fan. Further, in other embodiments, the outdoor fan 118 may comprise a mixed-flow fan, a centrifugal blower, and/or any other suitable type of fan and/or blower.

The outdoor metering device 120 may generally comprise a thermostatic expansion valve. In some embodiments, however, the outdoor metering device 120 may comprise an electronically-controlled motor driven EEV similar to indoor metering device 112, a capillary tube assembly, and/or any other suitable metering device. In some embodiments, while the outdoor metering device 120 may be configured to meter the volume and/or flow rate of refrigerant through the outdoor metering device 120, the outdoor metering device 120 may also comprise and/or be associated with a refrigerant check valve and/or refrigerant bypass configuration when the direction of refrigerant flow through the outdoor metering device 120 is such that the outdoor metering device 120 is not intended to meter or otherwise substantially restrict flow of the refrigerant through the outdoor metering device 120.

The reversing valve 122 may generally comprise a four-way reversing valve. The reversing valve 122 may also comprise an electrical solenoid, relay, and/or other device configured to selectively move a component of the reversing valve 122 between operational positions to alter the flow path of refrigerant through the reversing valve 122 and consequently the HVAC system 100. Additionally, the reversing valve 122 may also be selectively controlled by the system controller 106 and/or an outdoor controller 126.

The system controller 106 may generally be configured to selectively communicate with an indoor controller 124 of the indoor unit 102, an outdoor controller 126 of the outdoor unit 104, and/or other components of the HVAC system 100. In some embodiments, the system controller 106 may be configured to control operation of the indoor unit 102 and/or the outdoor unit 104. In some embodiments, the system controller 106 may be configured to monitor and/or communicate, directly or indirectly, with a plurality of sensors associated with components of the indoor unit 102, the outdoor unit 104, etc. The sensors may measure or detect a variety of parameters, such as, for example, pressure, temperature, and flow rate of the refrigerant as well as pressure and temperature of other components or fluids of or associated with HVAC system 100. In some embodiments, the HVAC system 100 may include a sensor (or plurality of sensors) for sensing or detecting the ambient outdoor temperature. Additionally, in some embodiments, the system controller 106 may be configured to control heating and/or cooling of zones associated with the HVAC system 100 (e.g., within the indoor space).

The system controller 106 may also be in communication with or incorporated with an input/output (I/O) unit 107 (e.g., a graphical user interface, a touchscreen interface, or the like) for displaying information and for receiving user inputs. The I/O unit 107 may display information related to the operation of the HVAC system 100 (e.g., from system controller 106) and may receive user inputs related to operation of the HVAC system 100. During operations, I/O unit 107 may communicate received user inputs to the system controller 106, which may then execute control of HVAC system 100 accordingly. Communication between the I/O unit 107 and system controller 106 may be wired, wireless, or a combination thereof. In some embodiments, the I/O unit 107 may further be operable to display information and receive user inputs tangentially and/or unrelated to operation of the HVAC system 100. In some embodiments, however, the I/O unit 107 may not comprise a display and may derive all information from inputs from remote sensors and remote configuration tools (e.g., remote computers, servers, smartphones, tablets, etc.). In some embodiments, system controller 106 may receive user inputs from remote configuration tools, and may further communicate information relating to HVAC system 100 to I/O unit 107. In these embodiments, system controller 106 may or may not also receive user inputs via I/O unit 107. In some embodiments, the system controller 106 and/or the I/O unit 107 may be embodied in a thermostat that may be disposed within the indoor space. As will be described in more detail below, such a thermostat (not specifically shown in FIG. 2) may include an onboard temperature sensor for determining the temperature of the indoor space during operations.

In some embodiments, the system controller 106 may be configured for selective bidirectional communication over a communication bus 128. In some embodiments, portions of the communication bus 128 may comprise a three-wire connection suitable for communicating messages between the system controller 106 and one or more of the HVAC system 100 components configured for interfacing with the communication bus 128. Still further, the system controller 106 may be configured to selectively communicate with HVAC system 100 components and/or any other device 130 via a communication network 132. In some embodiments, the communication network 132 may comprise a telephone network, and the other device 130 may comprise a telephone. In some embodiments, the communication network 132 may comprise the Internet, and the other device 130 may comprise a smartphone and/or other Internet-enabled mobile telecommunication device. In other embodiments, the communication network 132 may also comprise a remote server.

The indoor controller 124 may be carried by the indoor unit 102 and may generally be configured to receive information inputs, transmit information outputs, and/or otherwise communicate with the system controller 106, the outdoor controller 126, and/or any other device 130 via the communication bus 128 and/or any other suitable medium of communication. In some embodiments, the indoor controller 124 may be configured to communicate with an indoor personality module 134 that may comprise information related to the identification and/or operation of the indoor unit 102. In some embodiments, the indoor controller 124 may be configured to receive information related to a speed of the indoor fan 110, transmit a control output to an electric heat relay, transmit information regarding an indoor fan 110 volumetric flow-rate, communicate with and/or otherwise affect control over an air cleaner 136, and communicate with an indoor EEV controller 138. In some embodiments, the indoor controller 124 may be configured to communicate with an indoor fan controller 142 and/or otherwise affect control over operation of the indoor fan 110. In some embodiments, the indoor personality module 134 may comprise information related to the identification and/or operation of the indoor unit 102 and/or a position of the outdoor metering device 120.

The indoor EEV controller 138 may be configured to receive information regarding temperatures and/or pressures of the refrigerant in the indoor unit 102. More specifically, the indoor EEV controller 138 may be configured to receive information regarding temperatures and pressures of refrigerant entering, exiting, and/or within the indoor heat exchanger 108. Further, the indoor EEV controller 138 may be configured to communicate with the indoor metering device 112 and/or otherwise affect control over the indoor metering device 112. The indoor EEV controller 138 may also be configured to communicate with the outdoor metering device 120 and/or otherwise affect control over the outdoor metering device 120.

The outdoor controller 126 may be carried by the outdoor unit 104 and may be configured to receive information inputs, transmit information outputs, and/or otherwise communicate with the system controller 106, the indoor controller 124, and/or any other device 130 via the communication bus 128 and/or any other suitable medium of communication. In some embodiments, the outdoor controller 126 may be configured to communicate with an outdoor personality module 140 that may comprise information related to the identification and/or operation of the outdoor unit 104. In some embodiments, the outdoor controller 126 may be configured to receive information related to an ambient temperature associated with the outdoor unit 104, information related to a temperature of the outdoor heat exchanger 114, and/or information related to refrigerant temperatures and/or pressures of refrigerant entering, exiting, and/or within the outdoor heat exchanger 114 and/or the compressor 116. In some embodiments, the outdoor controller 126 may be configured to transmit information related to monitoring, communicating with, and/or otherwise affecting control over the compressor 116, the outdoor fan 118, a solenoid of the reversing valve 122, a relay associated with adjusting and/or monitoring a refrigerant charge of the HVAC system 100, a position of the indoor metering device 112, and/or a position of the outdoor metering device 120. The outdoor controller 126 may further be configured to communicate with and/or control a compressor drive controller 144 that is configured to electrically power and/or control the compressor 116.

System controller 106, indoor controller 124, and outdoor controller 126 (as well as compressor drive controller 144, indoor fan controller 142, indoor EEV controller 138, etc.) may each comprise any suitable device or assembly which is capable of receiving electrical (or other data) signals and transmitting electrical (or other data) signals to other devices. In particular, while not specifically shown, system controller 106, indoor controller 124, and outdoor controller 126 (as well as controllers 138, 142, 144, etc.) may each include a processor and a memory. The processors (e.g., microprocessor, central processing unit, or collection of such processor devices, etc.) may execute machine readable instructions (e.g., non-transitory machine readable medium) provided on the corresponding memory to provide the processor with all of the functionality described herein. The memory of each controller 106, 124, 126 may comprise volatile storage (e.g., random access memory), non-volatile storage (e.g., flash storage, read only memory, etc.), or combinations of both volatile and non-volatile storage. Data consumed or produced by the machine readable instructions can also be stored on the memory of controllers 106, 124, 126.

As shown in FIG. 1, the HVAC system 100 is configured for operating in a so called cooling mode in which heat may generally be absorbed by refrigerant at the indoor heat exchanger 108 and rejected from the refrigerant at the outdoor heat exchanger 114. Starting at the compressor 116, the compressor 116 may be operated to compress refrigerant and pump the relatively high temperature and high pressure compressed refrigerant through the reversing valve 122 and to the outdoor heat exchanger 114, where the refrigerant may transfer heat to an airflow that is passed through and/or into contact with the outdoor heat exchanger 114 by the outdoor fan 118. After exiting the outdoor heat exchanger 114, the refrigerant may flow through and/or bypass the outdoor metering device 120, such that refrigerant flow is not substantially restricted by the outdoor metering device 120. Refrigerant generally exits the outdoor metering device 120 and flows to the indoor metering device 112, which may meter the flow of refrigerant through the indoor metering device 112, such that the refrigerant downstream of the indoor metering device 112 is at a lower pressure than the refrigerant upstream of the indoor metering device 112. From the indoor metering device 112, the refrigerant may enter the indoor heat exchanger 108. As the refrigerant is passed through the indoor heat exchanger 108, heat may be transferred to the refrigerant from an airflow that is passed through and/or into contact with the indoor heat exchanger 108 by the indoor fan 110. Refrigerant leaving the indoor heat exchanger 108 may flow to the reversing valve 122, where the reversing valve 122 may be selectively configured to divert the refrigerant back to the compressor 116, where the refrigeration cycle may begin again.

Figure 2:
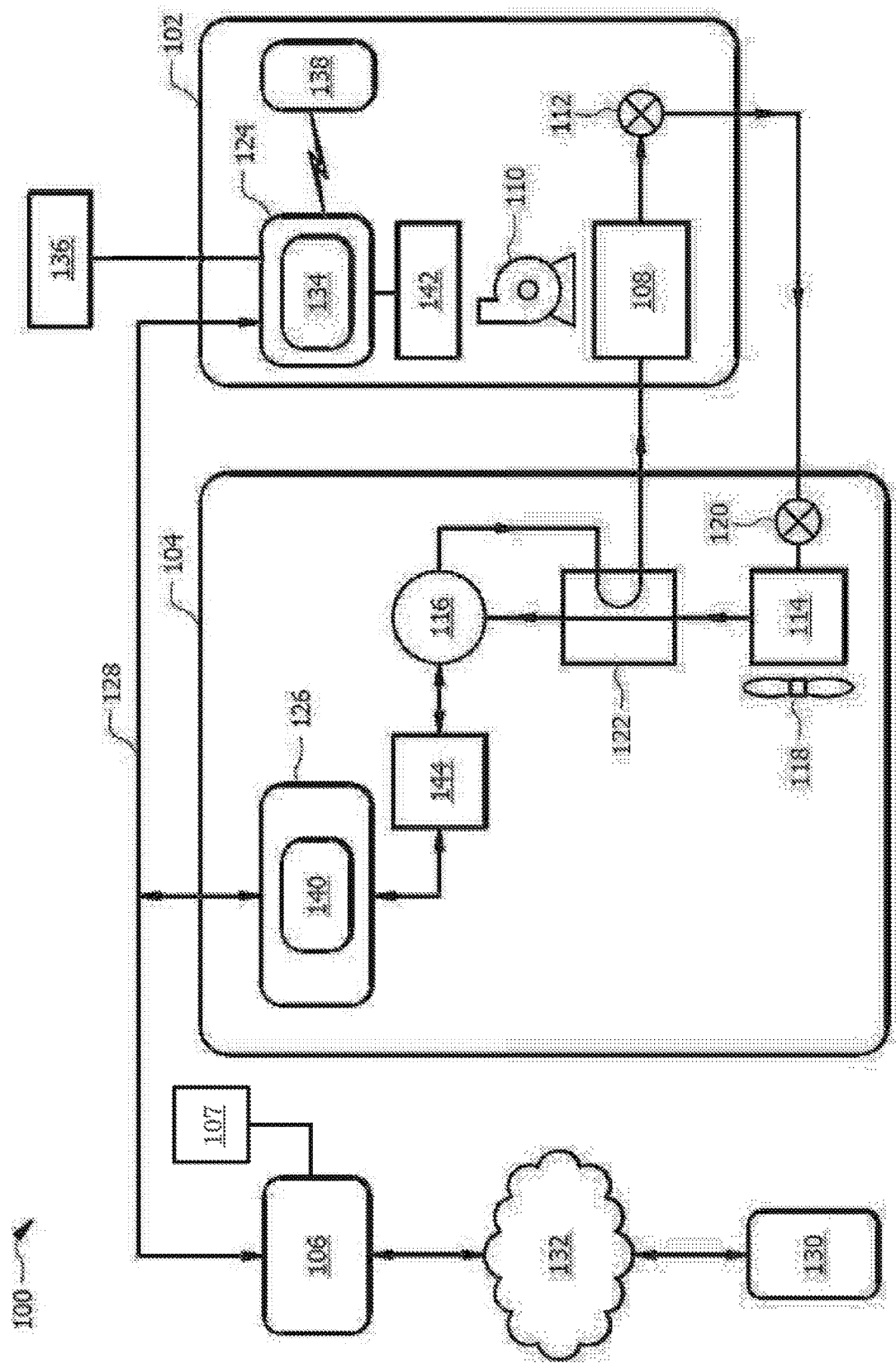
FIG. 2 is a diagram of the HVAC system of FIG. 1 configured for operating in a heating mode according to some embodiments.

Reference is now made to FIG. 2, which shows the HVAC system 100 configured for operating in a so-called heating mode. Most generally, the roles of the indoor heat exchanger 108 and the outdoor heat exchanger 114 are reversed as compared to their operation in the above-described cooling mode. For example, the reversing valve 122 may be controlled to alter the flow path of the refrigerant from the compressor 116 to the indoor heat exchanger 108 first and then to the outdoor heat exchanger 114, the outdoor metering device 120 may be enabled, and the indoor metering device 112 may be disabled and/or bypassed. In heating mode, heat may generally be absorbed by refrigerant at the outdoor heat exchanger 114 and rejected by the refrigerant at the indoor heat exchanger 108. As the refrigerant is passed through the outdoor heat exchanger 114, the outdoor fan 118 may be operated to move air into contact with the outdoor heat exchanger 114, thereby transferring heat to the refrigerant from the air surrounding the outdoor heat exchanger 114. Additionally, as refrigerant is passed through the indoor heat exchanger 108, the indoor fan 110 may be operated to move air into contact with the indoor heat exchanger 108, thereby transferring heat from the refrigerant to the air surrounding the indoor heat exchanger 108.

Figure 3:
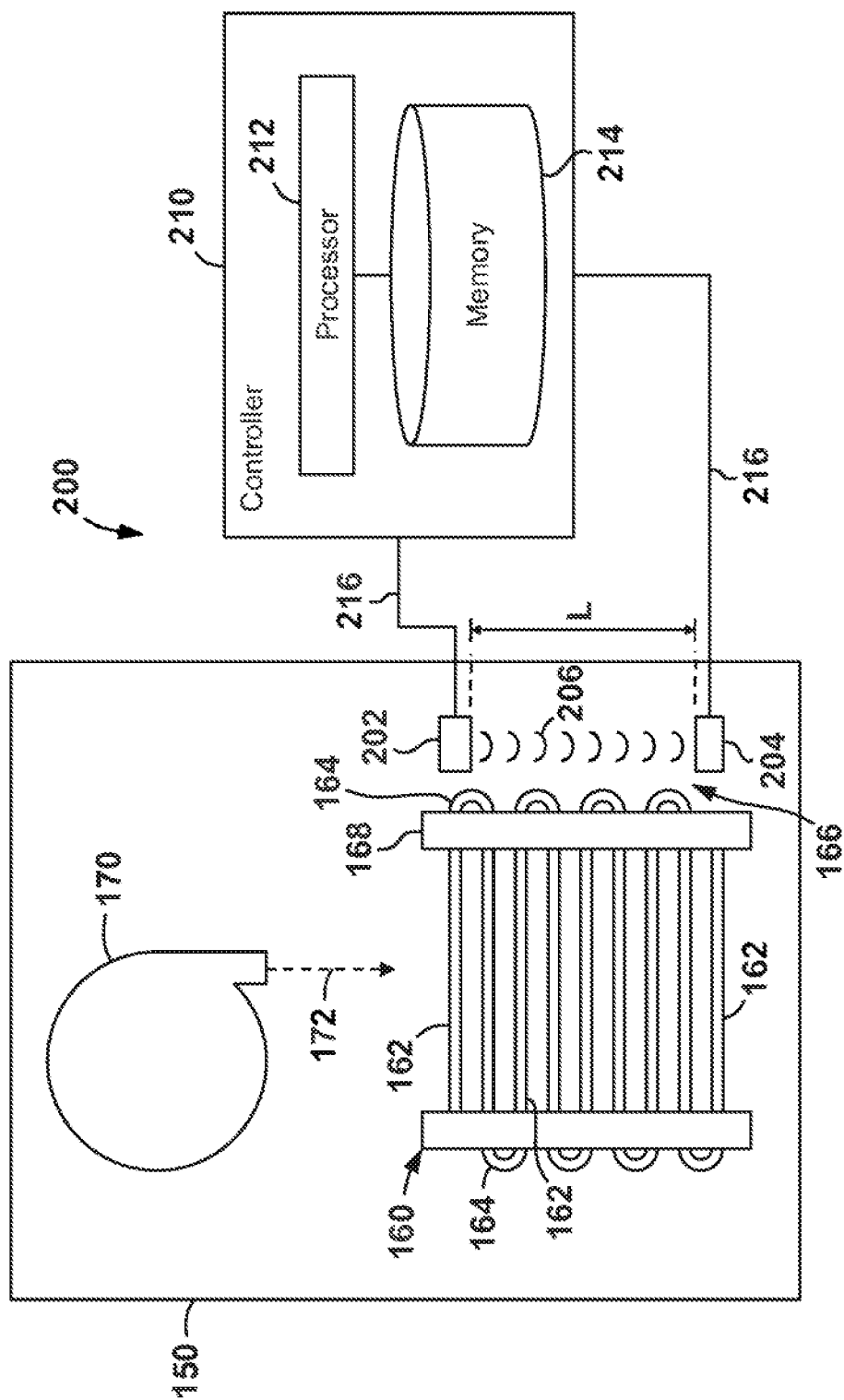
FIG. 3 is a diagram of an air handling unit and refrigerant leak detection system according to some embodiments.

Referring now to FIG. 3, a schematic diagram of an air unit 150 and a leak detection system 200 that may be used within a climate control system, such as, for instance, the HVAC system 100 of FIGS. 1 and 2, is shown. However, it should be appreciated that air unit 150 and leak detection system 200 may be utilized within a wide variety of climate control systems (e.g., such as those previously described above). Thus, any descriptions of the air unit 150 and leak detection system 200 within HVAC system 100 are merely meant to describe some potential implementations of the air unit 150 and leak detection system 200.

In some embodiments, the air unit 150 may generally serve as the indoor unit 102 or the outdoor unit 104 of HVAC system 100 in FIGS. 1 and 2. Accordingly, the air unit 150 includes a blower assembly 170 that is substantially similar to the previously described indoor fan 110 or outdoor fan 118 of FIGS. 1 and 2. Specifically, in some embodiments, the blower assembly 170 may generally comprise an electrically powered, motor driven rotatable blower that is configured to provide an airflow 172 through the air unit 150.

In addition, the air unit 150 includes a heat exchanger assembly 160 (which may be more simply referred to herein as "heat exchanger 160"). In some embodiments, the heat exchanger assembly 160 may be employed as the indoor heat exchanger 108 or the outdoor heat exchanger 114 within HVAC system 100 of FIGS. 1 and 2. The heat exchanger assembly 160 may be disposed within a fluid duct of the air unit 150 or otherwise be disposed proximate the blower assembly 170 so as to receive airflow 172 therethrough during operations. In some embodiments (e.g., such as the embodiment of FIG. 3), the blower assembly 170 is configured to direct airflow 172 from blower assembly 170 toward heat exchanger assembly 160. Thus, in this embodiment heat exchanger assembly 160 is downstream of blower assembly 172. In some embodiments, the blower assembly 170 is configured to pull an airflow (e.g., airflow 172) across heat exchanger such that blower assembly 170 is downstream of heat exchanger assembly 160.

The heat exchanger assembly 160 comprises a support structure or frame 168 that supports one or more conduits or tubes 162. The frame 168 may support tubes 162 in any suitable arrangement or shape. For instance, in some embodiments, heat exchanger assembly 160 may comprise an "A-coil" (or "A-frame") shape, a W-coil (or "W-frame") shape, an M-coil (or "M-frame") shape, an N-coil (or "N-frame") shape, an inverted N-Coil (or "inverted N-frame") shape, a V-coil (or "V-frame") shape, etc.

The tubes 162 are arranged in a plurality of rows, and the tubes of different rows (e.g., adjacent rows) may be fluidly coupled to one another so as to form one or more courses or flow paths through heat exchanger assembly 160 via the tubes 162. For example, the tubes 162 may be joined to one another with a plurality of joints 164 (which are generally shown as "Li-joints" in FIG. 3 but may comprise any suitable type or form of joint, such as, for instance hairpin joints). In other embodiments, the tubes 162 may be arranged in a plurality of parallel flow-paths and connected at each end of the heat exchanger assembly 160 by one or more headers or manifolds. The tubes 162 are connected to the joints 164 with brazing or other suitable connection methods.

During operations, tubes 162 may carry a refrigerant (e.g., a gas and/or liquid) that is configured to exchange heat with airflow 172 from blower assembly 170. The tubes 162 may generally be constructed of copper, stainless steel, aluminum, and/or another suitable material suitable for promoting heat transfer between the refrigerant carried within the tubes 162 and the airflow 172, during operations. The refrigerant may comprise any suitable heterogeneous or homogeneous fluid that is configured to exchange heat with airflow 172. In some embodiments refrigerant may comprise chlorofluorocarbons, hydrochlorofluorocarbons, hydrofluorocarbons, hydrocarbons, hydrofluoroolefins, etc. In some embodiments, the refrigerant may comprise a flammable material (e.g., propane). Some examples of a potentially flammable refrigerants which may be utilized within the embodiments disclosed herein include A2L refrigerants as classified by the American Society of Heating, Refrigeration and Air-Conditioning Engineers (ASHRAE) (e.g., difluoromethane, 1,3,3,3,-tetrafluoropropene etc.).

Referring still to FIG. 3, leak detection system 200 is coupled to air unit 150 and is configured to detect a leak of refrigerant from tubes 162 of heat exchanger assembly 160. Generally speaking, leak detection system 200 comprises an acoustic transmitter 202, an acoustic receiver 204, and a controller 210 coupled to the transmitter 202 and receiver 204. The acoustic transmitter 202 and acoustic receiver 204 are disposed within a space 166 within air unit 150 that may be outside and adjacent the tubes 162. Specifically, the space 166 may be disposed adjacent one or more of the joints 164. Without being limited to this or any other theory, the joints 164 may be the locations that present the highest likelihood of developing a leak during operations. Thus, in one embodiment, by placing transmitter 202 and receiver 204 within space 166 near the joints 164, leak detection system 200 may more readily and quickly detect a leak of refrigerant from the tubes 162 of heat exchanger assembly 160 during operations.

In some embodiments, the space 166 may be immediately adjacent or surrounding the tubes 162 (e.g., or joints 164 of tubes 162). For instance, the space 166 may be within 2 feet, 1 foot, 6 inches, etc. or less of tubes 162 and/or joints 164. Thus, if refrigerant is leaking from the tubes 162 (including joints 164), then the refrigerant should be released into the space 166 so as to be detected by leak detection system 200 in the manner described herein.

The transmitter 202 may comprise any device (or collection of devices) configured to emit an acoustic wave or signal 206. Specifically, in some embodiments, transmitter 202 is configured to convert an electrical signal into a corresponding acoustic wave or signal (e.g., acoustic wave 206). Receiver 204 may comprise any device (or collection of devices) configured to receive an acoustic wave or signal (e.g., such as acoustic wave 206). Specifically, in some embodiments, receiver 204 is configured to convert a received acoustic wave into a corresponding electrical signal. In some embodiments, transmitter 202 and/or receiver 204 may include piezoelectric components for converting acoustic waves to electrical signals and vice versa.

In some embodiments, the acoustic wave(s) 206 emitted by transmitter 202 and received by receiver 204 may have a frequency greater than 20 kilohertz (kHz), such as a frequency of approximately 40 kHz. Thus, the acoustic wave 206 may be referred to as an ultrasonic acoustic wave 206 (or more simply an "ultrasonic wave").

The transmitter 202 and receiver 204 are arranged (e.g., mounted) within air unit 150 such that the acoustic wave 206 is directed across the space 166 that is adjacent to joints 164 of heat exchanger assembly 160. In addition, the transmitter 202 and receiver 204 are mounted within air unit 150 such that they are separated by a distance L within space 166. Thus, acoustic wave(s) 206 traverse the distance L while traveling between transmitter 202 and receiver 204 during operations. Without being limited to this or any other theory, as the distance that the acoustic wave 206 travels between transmitter 202 and receiver 204 (e.g., distance L) increases, any changes in the time off light through the space 166 may be amplified. Thus, in some embodiments, the distance L may be increased as much as possible within the air unit 150 (e.g., depending on the available space within the unit 150)

so as to increase a resolution or accuracy of the time of flight detection for acoustic wave(s) 206.

Controller 210 is coupled to the transmitter 202 and receiver 204 via one or more conductive paths 216, which may comprise any suitable physical (e.g., cable, wire, lead, conductive trace, etc.) and/or wireless (e.g., WIFI, radio frequency (RF) communication, BLUETOOTH®, infrared, etc.) connection. As will be described in more detail below, during operations, controller 210 actuates transmitter 202 to direct acoustic waves 206 across the space 166 toward receiver 204 so as to determine whether a refrigerant is present within space 166 (thereby indicating a leak of refrigerant from tubes 162 of heat exchanger assembly 160).

Controller 210 may be a standalone controller within a climate control system (e.g., such as HVAC system 100 of FIGS. 1 and 2), and/or may be included, integrated, incorporated, etc. within any one or more of the other controllers that may be utilized to generally operate and control the climate control system (e.g., controllers 106, 124, 126, 138, 142, 144, I/O unit 107, etc. of HVAC system 100 in FIGS. 1 and 2). Generally speaking, controller 210 includes a processor 212 and a memory 214. The processor 212 (e.g., microprocessor, central processing unit, or collection of such processor devices, etc.) executes machine readable instructions (e.g., non-transitory machine readable instructions) provided on memory 214 to provide the processor 212 with all of the functionality described herein. The memory 214 may comprise volatile storage (e.g., random access memory), non-volatile storage (e.g., flash storage, read only memory, etc.), or combinations of both volatile and non-volatile storage. Data consumed or produced by the machine readable instructions can also be stored on memory 214. Controller 210 may also include or be coupled to a power source (not shown). The power source may comprise any suitable source of electrical power such as, for example, a battery, capacitor, a converter or transformer, wall plug, breaker box, etc.

During operations, controller 210 may cause or actuate transmitter 202 to emit an acoustic wave 206 (or a plurality of acoustic waves 206) across the space 166 toward receiver 204. Receiver 204 may then detect the acoustic wave 206 and send a signal (e.g., electrical signal) corresponding to the received acoustic wave 206 back to controller 210. Controller 210 may then analyze the received signal to determine a speed of sound through the space 166, a time of flight for the acoustic wave 206 between the transmitter 202 and receiver 204, or changes in either the speed of sound or time of flight. The determined speed of sound, time of flight, or changes therein may then be utilized to determine (e.g., infer) whether a refrigerant is present within the space 166. Specifically, in some embodiments controller 210 may determine a time of flight of the acoustic wave 206 between transmitter 202 and receiver 204 and then may calculate the speed of sound therebetween via the following computation:

$$S = L/\Delta t \quad (1),$$

where, S is the speed of sound in the space 166 (e.g., the speed of sound wave 206), Lit is the time of flight of wave 206 between transmitter 202 and receiver 204, and L is the distance between transmitter 202 and receiver 204.

The speed of sound may be influenced by the content of the medium through which the acoustic waves travel. Thus, without being limited to this or any other theory, the speed of sound through air may be different from the speed of sound through the refrigerant flowing through tubes 162 of heat exchanger assembly 160. Thus, if refrigerant is leaking from tubes 162 into the space 166, the speed of the acoustic waves 206 (and thus also their time of flight) will be altered from what one would expect if only air were present within space 166. In some specific embodiments, the speed of sound through the refrigerant may be less than the speed of sound through air, such that the time of flight for the acoustic waves 206 may be greater than that expected for when space 166 is only filled with air. Thus, if refrigerant is leaking from tubes 162 into the space 166, the speed of sound through the space 166 may be decreased from a value that may be expected when only air is present within the space 166. It should be appreciated that in some embodiments, the speed of sound may actually increase through the refrigerant (such that the time of flight would decrease). Accordingly, the changes in the speed of sound (and time of flight) may ultimately depend on the type of refrigerant utilized within the climate control system.

As may be appreciated within Equation (1) above, the speed of sound (S) is related to the time of flight (Lit) by the distance (L), and since the distance (L) may be fixed for the corresponding leak detection system 200. Accordingly, a determination of the presence of refrigerant within the space 166 based on the speed of sound, may also be based on the time of flight (e.g., between transmitter 202 and receiver 204). In some embodiments, the controller 210 may determine the presence of refrigerant within the space 166 based on the time of flight (Lit) alone (i.e., without additionally determining the speed of sound).

In some embodiments, controller 210 may determine whether the determined speed of sound is below a threshold, or whether the time of flight is above a threshold, or whether the magnitude of the difference between multiple speed of sound determinations (or multiple time of flight measurements) is above a threshold. In some embodiments, the threshold may comprise a value for the speed of sound (or time of flight) that is associated with a minimum concentration of refrigerant within the air of space 166. In particular, the threshold speed (or time) may be associated with a minimum concentration of refrigerant within space 166 that may indicate a leak. For instance, in some embodiments, the threshold may be a speed of sound within space 166 (or a time of flight between transmitter 202 and receiver 204) that is associated with a concentration of 2 vol. % or more of refrigerant within space 166. In some embodiments, the controller 210 may consult a look-up table with values of the speed of sound related to concentrations of the refrigerant (e.g., in vol. %) within the space 166.

Thus, by emitting acoustic waves 206 (e.g., such as ultrasonic acoustic waves) between transmitter 202 and receiver 204 and determining (e.g., via controller 210) the time of flight of the acoustic waves therebetween, a leak of refrigerant from heat exchanger assembly 160 into air unit 150 may be detected. In some embodiments, once a refrigerant leak has been detected via leak detection system 200, one or more corrective or protective measures may be taken. For instance, in some embodiments, if controller 210 determines that refrigerant is leaking into the space 166 (e.g., such as by determining that the speed of the sound wave(s) 206 is below the predetermined threshold as previously described), then controller 210 may cause or direct the blower assembly 170 initiate airflow 172. If the blower assembly 170 is already operating to drive airflow 172 when a leak is detected, the controller 210 cause or direct blower assembly 170 to increase the speed of the airflow 172. In particular, controller 210 may directly cause blower assembly 170 to increase the speed of airflow 172 or may send an appropriate signal to another controller (or controllers) within the associated climate control system (e.g., such as one or more of the controllers 106, 124, 126, 138, 142, 144 of HVAC system 100 shown in FIGS. 1 and 2). Without being limited to this or any other theory, by increasing the speed of airflow 172, the refrigerant leaked into the air unit 150 from heat exchanger assembly 160 may be more quickly diluted. For refrigerants that are flammable (e.g., such as A2L refrigerants described above), a relatively quick dilution is desirable so as to lower the risk of ignition of the refrigerant.

In some embodiments, controller 210 may cause or direct other components of an associated climate control system (e.g., HVAC system 100) to actuate based on the determination of a leak via leak detection system 200 as described above. For instance, in some embodiments, controller 210, upon detecting a refrigerant leak, may slow or stop the operation of a compressor (e.g., such as compressor 116 for HVAC system 100 in FIG. 1). As another example, in some embodiments, controller 210, upon detecting a refrigerant leak, may cause or direct a valve within the climate control system to close (e.g., partially or fully) so as to totally or partially stop the flow of refrigerant to the heat exchanger assembly 160 and/or isolate the location of the leak (e.g., such as by closing one or both of the valves 112, 120 of HVAC system 100 in FIG. 1).

In addition, in some embodiments controller 210 may issue an alarm upon determining that a refrigerant leak is occurring either in addition to or in lieu of taking other corrective actions. The alarm may include an audible and/or visual alarm to alarm persons disposed in and/or near the indoor space to the leak. The alarm may also include an electronic notification sent to one or more controllers or other devices within the climate control system and/or in a location remote from the climate control system (e.g., such as at a central monitoring station for monitoring operations or operational parameters of the climate control system).

In some embodiments, the controller 210 may direct the transmitter 202 to emit acoustic waves for reception by the receiver 204 on a periodic basis (e.g., every, 5, 10, 15, 30, 60 minutes, etc.), to determine whether refrigerant is present within the space 166 at regular times or intervals. In some embodiments, the controller 210 may direct transmitter 202 to continuously (or substantially continuously) emit acoustic waves that are received by receiver 204, to substantially continuously determine whether refrigerant is present within the space 166.

Figure 4:
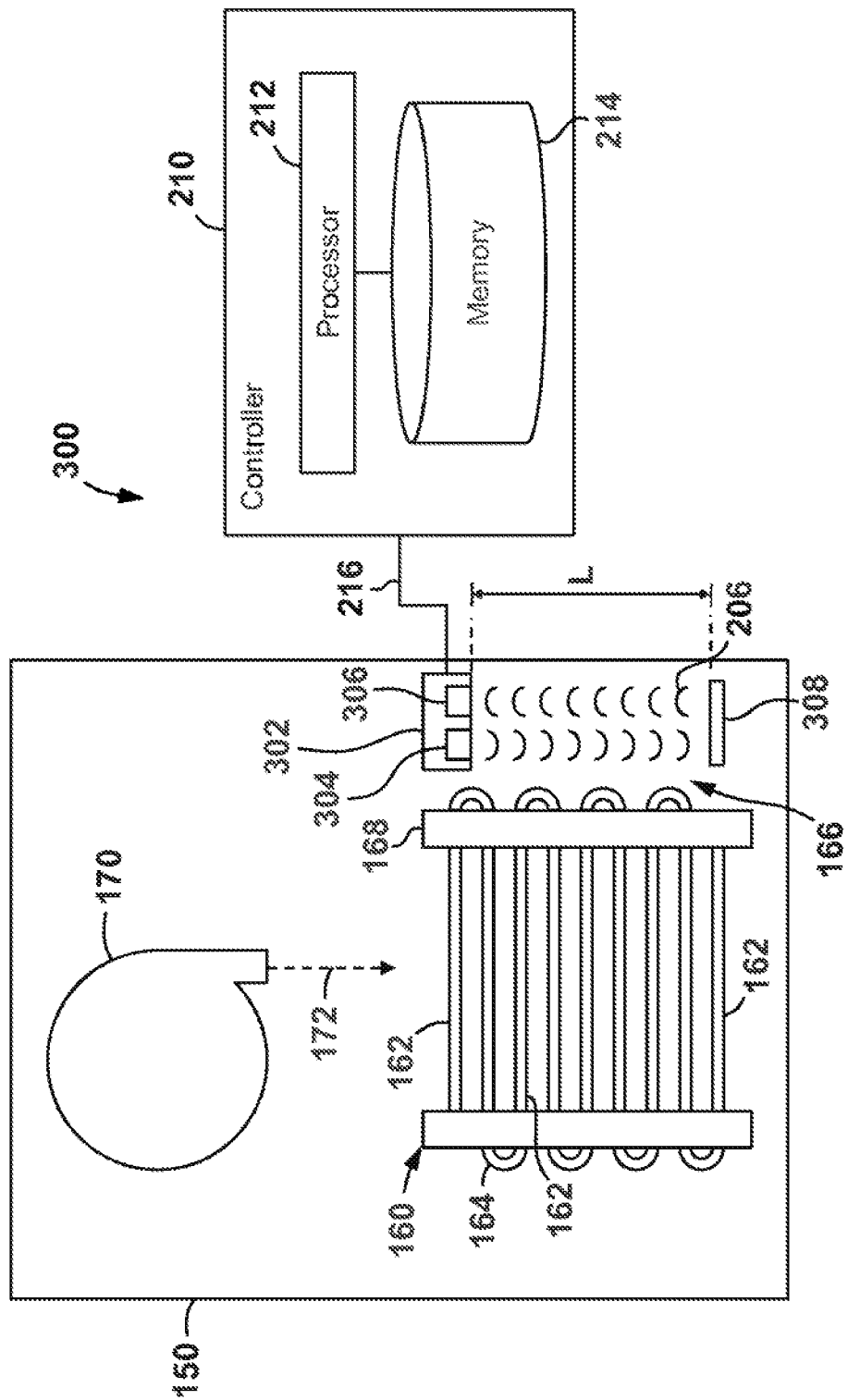
FIG. 4 is a diagram of an air handling unit and refrigerant leak detection system according to some embodiments.

Referring now to FIG. 4, a schematic diagram of air unit 150 and a refrigerant leak detection system 300 coupled thereto is shown. Leak detection system 300 may be generally similar to leak detection system 200 previously described. Thus, the features of leak detection system 300 that are shared with leak detection system 200 are identified with the same reference numerals, and the description below will focus on the features of leak detection system 300 that are different from leak detection system 200.

Leak detection system 300 includes controller 210. In addition, leak detection system 300 include a transceiver 302 and reflector 308 disposed within the space 166 of air unit 150 in place of transmitter 202 and receiver 204. The transceiver 302 includes a transmitter 304 and a receiver 306, which are substantially similar to the transmitter 202 and receiver 204 previously described above (see e.g., FIG. 3). Thus, during operations, transmitter 304 may emit acoustic waves 206 (e.g., periodically or substantially continuously as previously described) in response to received electrical signals (e.g., from controller 210), and receiver 306 may receive and convert acoustic waves 206 into corresponding electrical signals. Reflector 308 may comprise any device or surface that is configured to reflect an acoustic wave, such as acoustic waves 206 emitted from transmitter 304. In some embodiments, reflector 308 may comprise a wall or other structure within the air unit 150. As shown in FIG. 4, transceiver 302 and reflector 308 are separated by the distance L within space 166.

During operations, controller 210 may cause transmitter 304 to emit an acoustic wave 206 (or a plurality of acoustic waves 206) across the space 166 toward reflector 308 which then reflects the acoustic wave(s) 206 back toward receiver 306. Receiver 306 may then detect the acoustic wave(s) 206 and send a signal (e.g., electrical signal) corresponding to the received acoustic wave 206 back to controller 210. Controller 210 may then analyze the received signal to determine a time of flight of the acoustic wave 206 between transmitter 304 and receiver 306, a speed of sound through the space 166, or changes in the time or flight or speed of sound, etc., so as to determine (e.g., infer) whether a refrigerant is present within the space 166 in a similar manner to that described above for leak detection system 200. However, because the acoustic waves 206 are reflected off of reflector 308, the total distance traveled by the acoustic waves 206 may increase (e.g., double) compared to the distance the acoustic wave 206 travels between transmitter 202 and receiver 204 for system 200.

Specifically, controller 210 may determine a time of flight of the acoustic wave 206 between transmitter 304 and receiver 306 and then may calculate the speed of sound via the following computation:

$$S=(2L)/\Delta t \quad (2)$$

where, S is the speed of sound in the space 166 (e.g., the speed of sound wave 206), Lit is the time of flight of wave 206 between transmitter 304 and receiver 306, and L is the distance between transceiver 302 and reflector 308. Thus, because the acoustic waves 206 traverse the distance L twice between transmitter 304 and receiver 306, the distance L is multiplied by 2 in equation (2) above. Without being limited to this or any other theory, increasing the distance that the acoustic wave 206 travels between transmitter 304 and receiver 306 may allow any changes in the time of flight through the space 166 to be effectively amplified as previously described. Thus, by doubling the distance L as shown above in equation (2) above, the sensitivity, resolution, and/or accuracy of a leak determination may therefore be increased.

Once the speed of sound (or time of flight) is determined (e.g., via equation (2) above), controller 210 may determine whether refrigerant is leaking into the space 166 and, if so, may initiate appropriate corrective or responsive action in substantially the same manner as previously described above for leak detection system 200. Thus, these features are not repeated again in the interests of brevity.

Figure 5:
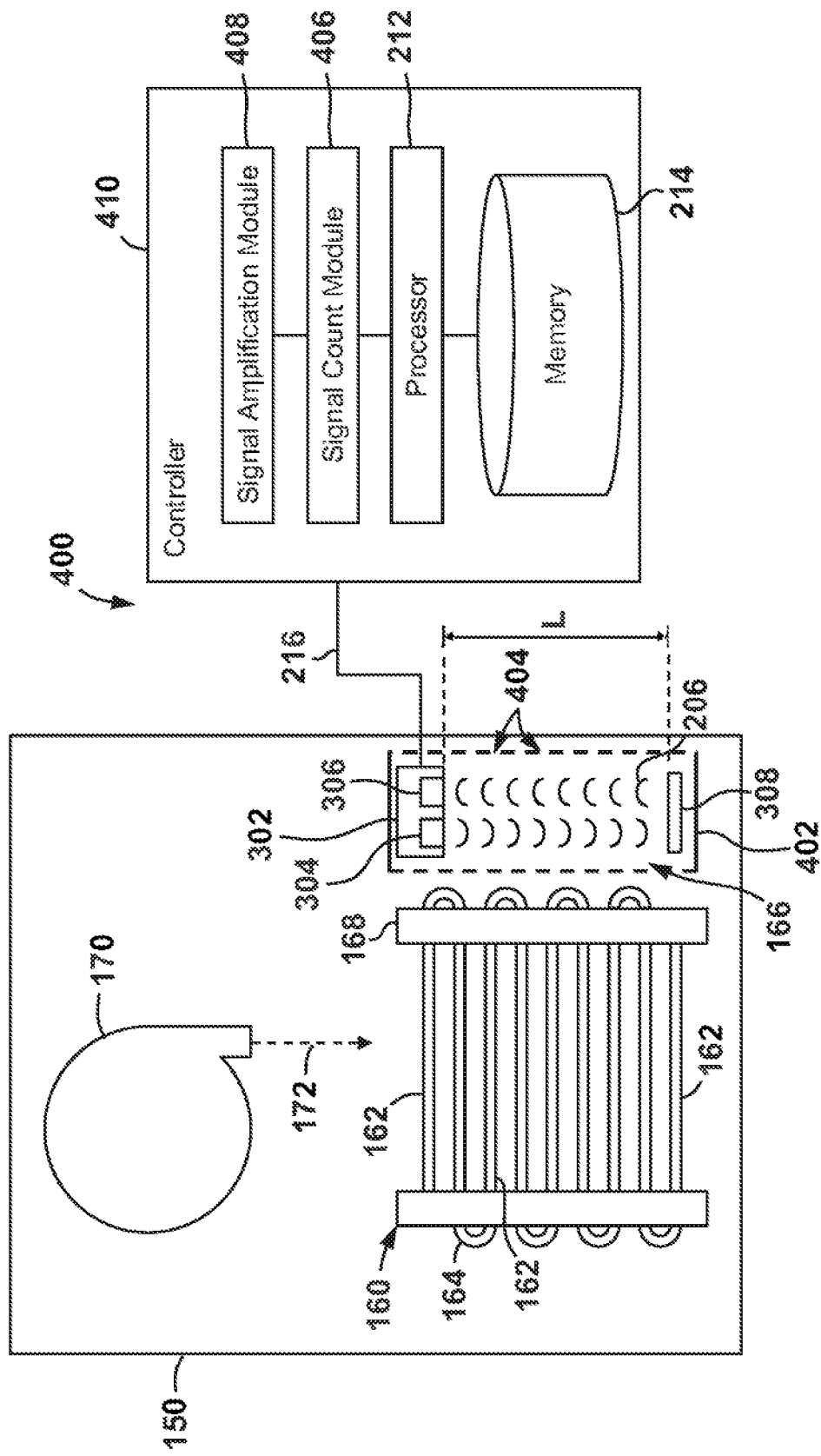
FIG. 5 is a diagram of an air handling unit and refrigerant leak detection system according to some embodiments.

Referring now to FIG. 5, a schematic diagram of air unit 150 and a refrigerant leak detection system 400 coupled thereto is shown. Leak detection system 400 may be generally similar to leak detection systems 200, 300 previously described. Thus, the features of leak detection system 400 that are shared with leak detection systems 200, 300 are identified with the same reference numerals, and the description below will focus on the features of leak detection system 400 that are different from leak detection systems 200, 300.

Leak detection system 400 includes controller 410 in place of controller 210 and additionally includes a reverberation chamber 402 disposed about transceiver 302 and reflector 308 within the space 166. The reverberation chamber 402 includes a plurality of perforations 404 such that fluids (e.g., air, refrigerant, etc.) disposed within air unit 150 may freely flow into and through reverberation chamber 402 during operations. In addition, reverberation chamber 402 may be configured to reflect acoustic waves (e.g., acoustic waves 206) therein such that an acoustic wave may be echoed a number of times through reverberation chamber 402. Thus, reverberation chamber 402 may be constructed of any suitable material that is configured to echo or reflect acoustic waves, such as, for instance, a metallic material.

Controller 410 includes processor 212 and memory 214, which are the same as previously described above. In addition, controller 410 also includes a signal amplification module 408 and a signal count module 406. Modules 406, 408 may comprise any suitable device, circuit, or assembly that is coupled to and/or disposed within controller 410 for carrying out the functionality described herein. In some embodiments, modules 406 and/or 408 may comprise machine readable instructions that are saved in memory 214 and executed by processor 212.

The signal amplification module 408 is configured to trigger or actuate transmitter 304 to emit an amplifying acoustic wave (e.g., acoustic wave 206) upon receipt of a reflected acoustic wave via the receiver 306. The subsequently emitted amplifying acoustic wave may have the same phase as the reflected acoustic wave received at the receiver 306, such that the subsequently emitted amplifying acoustic wave may amplify the reflected acoustic wave. In addition, the signal count module 406 may be configured to count or log a number of reflected acoustic waves received or detected by the receiver 306 during operations. In particular, the signal count module 406 may send an appropriate signal to the processor 212 when a predetermined number (e.g., 8, 10, 12, 14, 16, 18, 20, etc.) of reflected acoustic waves 206 are detected or received by the receiver 306.

During operations, an acoustic wave 206 is emitted by the transmitter 304 and directed across the reverberation chamber 402 toward reflector 308. In some embodiments, the reflector 308 may simply comprise a surface or the reverberation chamber 402. The reflector 308 and/or reverberation chamber 402 then cause the acoustic wave 206 to reflect back and forth between the transceiver 302 and reflector 308 a plurality of times. Each time the acoustic wave 206 is reflected back to the transceiver 302, receiver 306 receives or detects the echoed acoustic wave 206 and the signal amplification module 408 may actuate transmitter 304 to emit an amplifying acoustic wave that is in phase with the received acoustic wave 206 as previously described above. In addition, each time the receiver 306 receives or detects the echoed acoustic waves 206, the signal count module 406 may sum the received signals until the predetermined number of separate signals or echoes is received. Upon reaching the predetermined number of echoes, the signal count module 406 may send an appropriate signal (e.g., an overflow signal) to the processor 212 and a time of flight from the initial acoustic wave 206 emitted from transmitter 304 to the last received echo at receiver 306 is determined. In some embodiments, the processor 212 may then determine the speed of sound within the space 166 based on the determined time of flight.

Specifically, controller 410 may determine a time of flight of the echoed acoustic wave 206 between transmitter 304 and receiver 306 (and including all of the reflections and echoes within the reverberation chamber 402) and then may (in some embodiments) calculate the speed of sound therebetween via the following computation:

$$S = (X2L)/\Delta t \qquad (3)$$

where, S is the speed of sound in the space 166 (e.g., the speed of sound wave 206), Lit is the time of flight of wave 206 between transmitter 304 and receiver 306, L is the distance between transceiver 302 and reflector 308, and X is the predetermined number of echoes that the acoustic wave 206 experiences during the time of flight. Thus, because the acoustic waves 206 traverse the distance L twice with each echo within the reverberation chamber 402, the distance L is doubled and then multiplied by this number of echoes in equation (3) above.

Once the time of flight or speed of sound is determined (e.g., via equation (3) above), controller 410 may determine whether refrigerant is leaking into the space 166 and, if so, may initiate appropriate corrective or responsive action in substantially the same manner as previously described above for controller 210 in leak detection system 200. Thus, these features are not repeated again in the interests of brevity. However, the effective distance between the transmitter 304 and receiver 306 may be further increased as a result of the plurality of echoes of the acoustic wave 206 so as to further improve the accuracy of the leak determination within space 166 in the manner described above.

In some embodiments, controller 410 may not include the signal amplification module 408, such that acoustic wave amplification is not carried out during the above described operations. Other than this change, in these embodiments, the other features and functions of the remaining features of leak detection system 400 remain the same as that previously described above.

Figure 6:
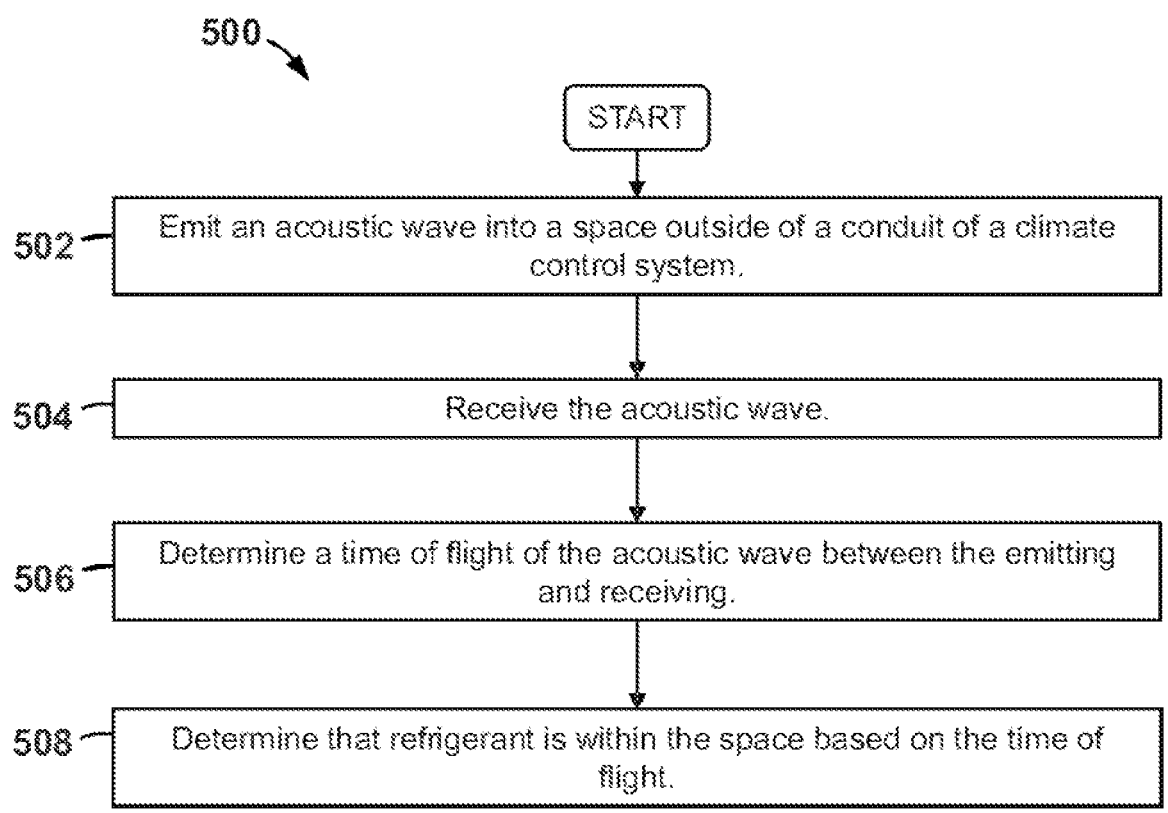
FIG. 6 is a flow chart of methods of detecting a refrigerant leak from a climate control system according to some embodiments.

Referring now to FIG. 6, a method 500 of detecting a refrigerant leak from a climate control system is shown. Method 500 may be performed (e.g., at least partially) via the leak detection systems 200, 300, 400, previously described above. Thus, in describing the features of method 500, reference may be made to leak detection systems 200, 300, 400 so as to explain some possible examples of method 500. However, it should be appreciated that method 500 may be performed utilizing systems that are different from leak detection systems 200, 300, 400 previously described.

Method 500 includes emitting an acoustic wave into a space outside a conduit of a climate control system at 502 and receiving the acoustic wave at 504. For instance, as previously described above, a refrigerant may be flowed or contained within tubes 162 of heat exchanger assembly 160 for the air unit 150 of FIGS. 3-5. The refrigerant may comprise any suitable fluid (e.g., gas, liquid, etc.) that is configured to exchange thermal energy with another fluid (e.g., such as airflow 172 emitted from blower assembly 170 as previously described). Thus, refrigerant may comprise any of the example refrigerants discussed above. The acoustic wave may be emitted at 502 and received at 504 within a space that is adjacent, such as immediately adjacent the conduit (e.g., within 1 foot of the conduit, or 6 inches of the conduit, etc.). In some embodiments, the acoustic wave may be emitted at 502 and received at 504 in a space adjacent or surrounding a joint (e.g., joints 164) of the conduit.

In some embodiments, the acoustic wave emitted at 502 and received at 504 may comprise an ultrasonic acoustic wave that includes a frequency greater than 20 kHz, such as about 40 kHz. In some embodiments, the acoustic wave may be emitted by a suitable transmitter, such as, for instance the standalone transmitter 202 shown in FIG. 3 or a transmitter included within a transceiver such as the transmitter 304 of transceiver 302 shown in FIGS. 4 and 5. In addition, in some embodiments, the acoustic wave may be received by a suitable receiver at 504, such as, for instance the standalone receiver 204 shown in FIG. 3 or a receiver included within a transceiver such as the receiver 306 of transceiver 302 shown in FIGS. 4 and 5.

Following receipt of the acoustic wave at 504, method 500 proceeds to 506 to determine the time of flight of the acoustic wave between the emitting and receiving at 502 and 504, respectively. Next, method 500 includes determining that refrigerant is within the space based on the time of flight at 508. In some embodiments, the determination at 508 may comprise determining that the time of flight is above or below a threshold as appropriate depending on the characteristics of the particular refrigerant as previously described above. In some embodiments, the determination at 508 may comprise determining the speed of sound within the space and then determining that the speed of sound is above or below a threshold. In some of these embodiments, the speed of sound may be determined using one of equations (1), (2), or (3) above (e.g., such as when the leak detection systems 200, 300, 400, respectively, are being utilized to perform method 500). In some embodiments, the determination at 508 may comprise determining that the time of flight or speed of sound is above or below a threshold that is associated with a minimum concentration of refrigerant within the space so as to indicate a leak of the refrigerant from the conduit. For instance, as previously described above, in some embodiments, the speed of sound through the refrigerant may be less than the speed of sound through air (such that the time of flight would be increased). Thus, if the speed of sound through the space falls below a predetermined threshold (or if the time of flight rises above a predetermined threshold), it may indicate that some minimum amount or concentration of refrigerant is present within the space, thereby indicating that the refrigerant is leaking from the conduit.

In some embodiments, method 500 may also include reflecting the emitting acoustic wave before receiving the acoustic wave at 504. For example, as previously described above, the emitted acoustic wave may be reflected off of a reflector or reflective surface (e.g., reflector 308) to increase a travel distance of the acoustic wave and thereby improve an accuracy of the determined speed of sound. In addition, in some embodiments, method 500 may also include reflecting the acoustic wave within a reverberation chamber, such as the reverberation chamber 402 shown in FIG. 5 and described above. In some of these embodiments, the method 500 may include detecting a plurality of echo or reflections of the acoustic wave and determining the speed of sound based on the time of flight of the plurality of detected echoes or reflections. In addition, other embodiments of method 500 may include a variety of other features and steps, such as any of those described above for the leak detection systems 200, 300, 400, etc.

Embodiments disclosed herein include systems and methods for detecting a refrigerant leak from a climate control system (e.g., leak detection systems 200, 300, 400, method 500, etc.). Specifically, the systems and methods disclosed herein may determine the presence of a leak by monitoring the speed of sound through a space surrounding a refrigerant-containing conduit of the climate control system (e.g., space 166 within air unit 150) or a time of flight of an acoustic wave (e.g., wave 206) through the space. Accordingly, through use of the disclosed systems and methods, a refrigerant leak may be recognized relatively early such that appropriate actions (e.g., repairs, system operations, etc.) may take place so as to avoid or reduce the negative consequences associated with such a leak.

While exemplary embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the disclosure. Accordingly, the scope of protection is not limited to the embodiments described herein, but is only limited by the claims that follow, the scope of which shall include all equivalents of the subject matter of the claims. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simplify subsequent reference to such steps.

What is claimed is:

1. A refrigerant leak detection system for a climate control system, the system comprising:
   an air unit comprising a housing and a heat exchanger including a conduit, the conduit including one or more joints and configured to carry a refrigerant of the climate control system, and a space located within the housing and outside the conduit;
   a transmitter located within the space and adjacent the heat exchanger, the transmitter configured to emit an acoustic wave within the space and direct the acoustic wave to travel adjacent to at least one joint of the conduit;
   a receiver located within the space and adjacent the heat exchanger, the receiver configured to detect the acoustic wave traveling within the space; and
   a controller coupled to the transmitter and the receiver, wherein the controller is configured to:
     determine a time of flight for the acoustic wave between the transmitter and the receiver; and
     determine whether the refrigerant is present in the space based on the time of flight.

2. The refrigerant leak detection system of claim 1, wherein the housing has a first side and a second side,
   wherein the second side is opposite the first side,
   wherein the transmitter and the receiver are arranged such that the acoustic waves are directed across the space from the first side to the second side.

3. The refrigerant leak detection system of claim 1, comprising:
   a transceiver located within the space and adjacent the heat exchanger, the transceiver including the transmitter and the receiver; and
   a reflector located within the space, the reflector configured to reflect the acoustic wave from the transmitter toward the receiver.

4. The refrigerant leak detection system of claim 3, comprising a reverberation chamber comprising a plurality of perforations, wherein the transceiver and the reflector are disposed within the reverberation chamber.

5. The refrigerant leak detection system of claim 3, wherein the transmitter is configured to emit the acoustic wave into the reverberation chamber such that the acoustic wave is reflected across the reverberation chamber to impact the receiver; and
   wherein the controller is configured to determine a speed of sound based on a time of flight of the acoustic wave after it has reflected across the reverberation chamber to impact the receiver a predetermined number of times.

6. The refrigerant leak detection system of claim 1, wherein the controller is configured to determine a speed of sound using the following computation:

$$S = \frac{(X2L)}{\Delta T},$$

where S is the speed of sound in the space, L is a distance between the transmitter, X is a predetermined number of echoes that the acoustic wave experiences during the time of flight and the receiver, and $\Delta T$ is the time of flight.

7. The refrigerant leak detection system of claim 1, wherein the controller is configured to determine that refrigerant is present in the space when the determined time of flight is above a threshold.

8. The refrigerant leak detection system of claim 1, wherein the controller is configured to initiate an increase in a speed of airflow within the climate control system as a result of determining that refrigerant is present in the space.

9. The refrigerant leak detection system of claim 1, wherein the controller is configured to cause an actuation of a valve or a change in a speed of a compressor of the climate control system as a result of determining that refrigerant is present in the space.

10. The refrigerant leak detection system of claim 1, wherein the acoustic wave has a frequency greater than 20 kilohertz (kHz).

11. A method of detecting a refrigerant leak from a climate control system, the method comprising:
(a1) emitting an acoustic wave from a transmitter into a space located within a housing of an air unit, the air unit including a heat exchanger with a conduit, the conduit including one or more joints configured to carry a refrigerant of the climate control system, wherein the transmitter is located within the housing and adjacent the heat exchanger;
(a2) directing the acoustic wave to travel adjacent at least one joint of the conduit
(b) receiving the acoustic wave at a receiver, wherein the receiver is located within the housing and adjacent the heat exchanger;
(c) determining a time of flight between (a) and (b); and
(d) determining that refrigerant is within the space as a result of the time of flight.

12. The method of claim 11, comprising reflecting the acoustic wave off of a reflector after (a) and before (b).

13. The method of claim 11, wherein (a) comprises emitting the acoustic wave into a perforated reverberation chamber disposed within the space;
wherein (b) comprises receiving a plurality of reflections of the acoustic wave within the reverberation chamber; and
wherein (c) comprises determining the time of flight between (a) and when a final reflection of the plurality of reflections is received during (b).

14. The method of claim 11, wherein (c) comprises determining a speed of sound using the following computation:

$$S = \frac{(X2L)}{\Delta T},$$

where S is the speed of sound in the space, L is a distance between the transmitter, X is a predetermined number of echoes that the acoustic wave experiences during the time of flight and the receiver, and $\Delta T$ is the time of flight.

15. The method of claim 11, wherein (d) comprises determining that the time of flight is above a threshold.

16. The method of claim 15, further comprising:
(e) increasing a speed of air flowing across the conduit as a result of the determination in (d).

17. The method of claim 11, further comprising:
actuating a valve or changing a speed of a compressor of the climate control system as a result of the determination in (d).

18. The method of claim 11, wherein the acoustic wave has a frequency above 20 kHz.

* * * * *